United States Patent [19]

Seaman et al.

[11] Patent Number: 5,100,886
[45] Date of Patent: Mar. 31, 1992

[54] METAL COMPLEXES OF PYRIDYL CYCLOPROPANE CARBOXAMIDE COMPOUNDS WHICH ARE USEFUL AS FUNGICIDES

[75] Inventors: David Seaman, Tunbridge Wells; Ian R. Matthews, Wokingham, both of England; Neal R. Bird, Richmond, Calif.

[73] Assignee: Imperial Chemical Industries PLC, London, England

[21] Appl. No.: 610,610

[22] Filed: Nov. 8, 1990

[30] Foreign Application Priority Data

Dec. 18, 1989 [GB] United Kingdom ............... 8928547

[51] Int. Cl.$^5$ .................. A61K 31/44; C07D 213/02
[52] U.S. Cl. ........................................ 514/188; 546/12
[58] Field of Search ............. 546/8, 9, 12; 514/352, 514/277, 188

[56] References Cited

U.S. PATENT DOCUMENTS

| | | | |
|---|---|---|---|
| 3,376,309 | 4/1968 | Foster et al. | 546/309 |
| 3,467,753 | 9/1969 | Foster et al. | 546/309 |
| 3,493,555 | 2/1970 | Wilbert et al. | 546/309 |
| 4,766,134 | 8/1988 | Baker et al. | 514/346 |
| 4,808,600 | 2/1989 | Baker et al. | 514/346 |
| 4,895,858 | 1/1990 | Baker et al. | 514/352 |

FOREIGN PATENT DOCUMENTS 2056974  7/1990  United Kingdom .

Primary Examiner—C. Warren Ivy
Assistant Examiner—Zinna Northington Davis
Attorney, Agent, or Firm—Lynn Marcus-Wyner

[57] ABSTRACT

A metal complex having the general formula (I):

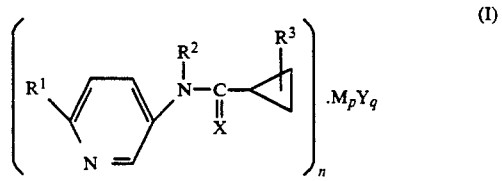

wherein $R^1$ is $C_{1-4}$ alkoxy, $C_{1-4}$ haloalkoxy, or $C_{2-4}$ alkenyloxy; $R^2$ is hydrogen or cyano; $R^3$ is hydrogen or methyl; X is oxygen or sulphur; $M_pY_q$ is a transition metal salt wherein M is a transition metal cation, Y is an anion and p and q are independently 1, 2 or 3 according to valency requirements; and n is 1 or 2. The metal complexes of formula (I) are active as fungicides.

12 Claims, No Drawings

METAL COMPLEXES OF PYRIDYL CYCLOPROPANE CARBOXAMIDE COMPOUNDS WHICH ARE USEFUL AS FUNGICIDES

The present invention relates to metal complexes of pyridyl cyclopropane carboxamides that are useful as fungicides, to a process for preparing them, to fungicidal compositions containing them and to methods of using them to combat fungi, especially fungal infections in plants.

Pyridyl cyclopropane carboxamides having the general formula (A):

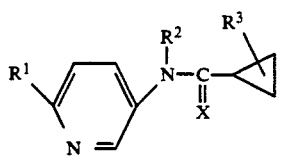

wherein $R^1$ is halogen, $C_{1-3}$ alkoxy or $C_{1-3}$ haloalkoxy; $R^2$ is hydrogen or cyano; $R^3$ is hydrogen or methyl; and X is oxygen or sulphur are disclosed in EP-A-0243971.

According to the present invention there is provided a metal complex having the general formula (I):

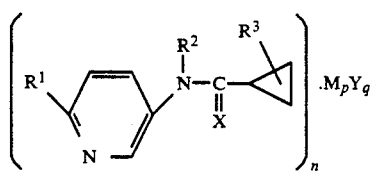

wherein $R^1$ is $C_{1-4}$ alkoxy, $C_{1-4}$ haloalkoxy, or $C_{2-4}$ alkenyloxy; $R^2$ is hydrogen or cyano; $R^3$ is hydrogen or methyl; X is oxygen or sulphur; $M_pY_q$ is a transition metal salt wherein M is a transition metal cation, Y is an anion and p and q are independently 1, 2 or 3 according to valency requirements; and n is 1 or 2.

The alkyl group and the alkyl moieties of alkoxy and haloalkoxy groups contain from 1 to 4 carbon atoms and are either straight or branched chain groups, for example, methyl, ethyl, n-propyl, iso-propyl, iso-butyl or tert-butyl.

The alkenyl moiety of the alkenyloxy group contains from 2 to 4 carbon atoms and is alk-1 enyl, alk-2-enyl or alk-3-enyl, for example, vinyl, allyl, 2-prop-1-enyl or 1-prop-1-enyl.

Halogen includes fluorine, chlorine, bromine and iodine.

$M_pY_q$ is a transition metal salt wherein M is a transition metal cation which is, for example, copper(II) or zinc(II), Y is an anion which is, for example, chloride, bromide, iodide, fluoride, nitrate, sulphate, acetate, phosphate, formate, citrate, tartrate, benzoate, borate, lactate or the anion of saccharin (o-benzoic sulphimide) and p and q are independently 1, 2 or 3 according to valency requirements. Examples of $M_pY_q$ are $CuCl_2$ and $ZnCl_2$.

In one particular aspect the invention provides a compound of formula (I) wherein $R^1$ is $C_{1-4}$ alkoxy; $R^2$ and $R^3$ are both hydrogen; X is oxygen; $M_pY_q$ is a transition metal salt wherein M is a copper (II) or zinc (II) cation, Y is a chloride, bromide, iodide, fluoride, nitrate, sulphate, acetate, phosphate, formate, citrate, tartrate, benzoate, borate, lactate or o-benzoic sulphimide anion and p and q are independently 1, 2 or 3 according to valency requirements; and n is 1, 2 or 3.

In a further aspect the invention provides a compound of formula (I) wherein $R^1$ is methoxy; $R^2$ and $R^3$ are both hydrogen; X is oxygen; $M_pY_q$ is a transition metal salt wherein M is a copper (II) or zinc (II) cation, Y is a chloride, bromide, iodide, fluoride, nitrate, sulphate, acetate, phosphate, formate, citrate, tartrate, benzoate, borate, lactate or o-benzoic sulphimide anion and p and q are independently 1, 2 or 3 according to valency requirements; and n is 1, 2 or 3.

In a still further aspect the invention provides a compound of formula (I) wherein $R^1$ is methoxy; $R^2$ and $R^3$ are both hydrogen; X is oxygen; $M_pY_q$ is copper(II) chloride or zinc(II) chloride; and n is 2.

In another aspect the invention provides a compound of formula (I) in which $R^1$ is $C_{1-4}$ alkoxy (especially methoxy), $R^2$ and $R^3$ are hydrogen, X is oxygen, M is copper(II) or zinc(II), Y is chloride, and n is 2.

Examples of compounds (I) according to the invention are given in Table I.

TABLE I

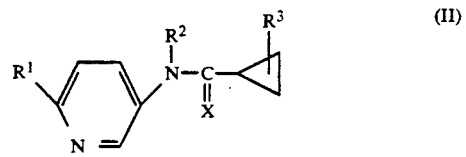

| Compound No. | $R^1$ | $R^2$ | $R^3$ | X | n | $M_pY_q$ | m.pt °C. |
|---|---|---|---|---|---|---|---|
| 1 | $OCH_3$ | H | H | O | 2 | $CuCl_2$ | 186–188 |
| 2 | $OCH_3$ | H | H | O | 2 | $ZnCl_2$ | 219–221 |

The compounds of general formula (I) can be prepared by reacting a compound of general formula (II):

(II)

wherein $R^1$, $R^2$, $R^3$ and X are as defined above, with a transition metal salt of formula $M_pY_q$, wherein M, Y, p and q are as defined above (such as copper(II) chloride or zinc(II) chloride), in a suitable solvent (such as aqueous ethanol).

The preparation of compounds of formula (II) is described in EP-A-0243971.

In a further aspect the invention comprises a process for preparing the metal complexes of formula (I).

The compounds of the invention are active fungicides and may be used to control one or more of the following pathogens:

*Pyricularia oryzae* on rice.

*Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants.

*Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines.

*Helminthosporium* spp., *Rhynchosporium* spp., *Septoria* spp., *Pyrenophora* spp., *Pseudocercosporella herpotrichoides* and *Gaeumannomyces graminis* on cereals.

*Cercospora arachidicola* and *Cercosporidium personata* on peanuts and other *Cercospora* species on other hosts, for example, sugar beet, bananas, soya beans and rice.

*Botrytis cinerea* (grey mould) on tomatoes, strawberries, vegetables, vines and other hosts.

*Alternaria* spp. on vegetables (e.g. cucumber), oil-seed rape, apples, tomatoes and other hosts.

*Venturia inaequalis* (scab) on apples.

*Plasmopara viticola* on vines.

*Thanatephorus cucumeris* on rice and other *Rhizoctonia* species on various hosts such as wheat and barley, vegetables, cotton and turf.

Some of the compounds show a broad range of activities against fungi in vitro. They may also have activity against various post-harvest diseases of fruit (e.g. *Penicillium digitatum* and *italicum* and *Trichoderma viride* on oranges, *Gloeosporium musarum* on bananas and *Botrytis cinerea* on grapes).

Further, some of the compounds may be active as seed dressings against *Fusarium* spp., *Septoria* spp., *Tilletia* spp., (bunt, a seed-borne disease of wheat), *Ustilago* spp. and *Helminthosporium* spp. on cereals, *Rhizoctonia solani* on cotton and *Pyricularia oryzae* on rice.

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems The invention compounds may also be injected into plants or sprayed onto vegetation using electrodynamic spraying techniques or other low volume methods The term "plant" as used herein includes seedlings, bushes and trees. Furthermore, the fungicidal method of the invention includes preventative, protectant, prophylactic and eradicant treatments The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be performed granules suitable for application to the soil without further treatment These granules can be made either by impregnating pellets of filler with the active ingredient or by pelleting a mixture of the active ingredient and powdered filler Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone, and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I).

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds example, sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as *Septoria*, *Gibberella* and *Helminthosporium* spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are (RS)-1-aminopropylphosphonic acid, (RS)-4-(4-chlorophenyl)-2-phenyl-2-(1H-1,2,4-triazol-1-yl-methyl)butyronitrile, (Z)-N-but-2-enyloxymethyl-2-chloro-2',6'-diethylacetanilide, 1-(2-cyano-2-methoxyiminoacetyl)-3-ethyl urea, 1-[(2RS,4RS;2RS,4RS)-4-bromo-2-( 2,4-dichlorophenyl)tetrahydrofurfuryl]-1H-1,2,4-triazole, 3-(2,4-dichlorophenyl)-2-(1H-1,2,4-triazol-1-yl)-quinazolin-4(3H)-one, 3-chloro-4-[4-methyl-2-(1H-1,2,4-triazol-1-methyl)-1,3-dioxolan-2-yl]phenyl-4-chlorophenyl ether, 3-chloro-5-ethylsulphinylthiophene-2,4-dicarbonitrile, 4-bromo-2-cyano-N,N-dimethyl-6-trifluoromethylbenz-imidazole-1-sulphonamide, 5-ethyl-5,8-dihydro-8-oxo(1,3)dioxolo(4,5-g)quinoline-7 carboxylic acid, α-[N-(3-chloro-2,6-xylyl)-2-methoxyacetamido]-γ-butyrolactone, aldimorph, anilazine, BAS 454, benalaxyl, benomyl, biloxazol, binapacryl, bitertanol, blasticidin S, bupirimate, buthiobate, captafol, captan, carbendazim, carboxin, chlorbenz-thiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1'-dioxide, dichlofluanid, dichlone, diclobutrazol, diclomezine, dicloran, difenoconazole, dimethamorph, dimethirimol, diniconazole, dinocap, ditalimfos, dithianon, dodemorph, dodine, edifenphos, etaconazole, ethirimol, ethyl (Z)-N-benzyl-N-([methyl(methylthioethylideneaminooxycarbonyl)amino]thio)-β-alaninate, etridiazole, fenapanil, fenarimol, fenfuram, fenpiclonil, fenpropidin, fenpropimorph, fentin acetate, fentin hydroxide, flutolanil, flutriafol, flusilazole, folpet, fosetyl-aluminium, fuberidazole, furalaxyl, furconazole-cis, guazatine, hexaconazole, hydroxyisoxazole, imazalil, imibenconazole, iprobenfos, iprodione, isoprothiolane, kasugamycin, mancozeb, maneb, mepanipyrim, mepronil, metalaxyl, methfuroxam, metsulfovax, myclobutanil, N (4-methyl-6-prop-1-ynylpyrimidin-2-yl)aniline, neoasozin, nickel dimethyldithiocarbamate, nitrothalisopropyl, nuarimol, ofurace, organomercury compounds, oxadixyl, oxycarboxin, pefurazoate, penconazole, pencycuron, phenazin oxide, phthalide, polyoxin D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, streptomycin, sulphur, tebuconazole, techlofthalam, tecnazene, tetraconazole, thiabendazole, thiophanate-methyl, thiram, tolclofos-methyl, triacetate salt of 1,1'-iminodi(octamethylene)diguanidine, triadimefon, triadimenol, triazbutyl, tricyclazole, tridemorph, triforine, validamycin A, vinclozolin, zarilamid and zineb. The compounds of general formula (I) can be mixed with soil, peat or other rooting media for the protection of plants against seed-borne, soil-borne or foliar fungal diseases.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophos, phenthoate, pirimicarb, propaphos and XMC.

Plant growth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl)-4,6-di-methyl-2-oxo-1,2-dihydropyridine-3-carboxylic acid, methyl-3,6-dichloroanisate, abscisic acid, asulam, benzoylprop-ethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodobenzoic acid), substituted quaternary ammonium and hosphonium compounds (e.g. chloromequat, chlorphonium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. $GA_3$, $GA_4$ or $GA_7$) and triapenthenol.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophas, phenthoate, pirimicarb, propaphos and XMC.

Plant growth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl)-4,6-di-methyl-2-oxo-1,2-dihydropyridine-3-carboxylic acid, methyl-3,6-dichloroanisate, abscisic acid, asulam, benzoylprop-ethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodobenzoic acid), substituted quaternary ammonium and phosphonium compounds (e.g. chloromequat, chlorphonium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. $GA_3$, $GA_4$ or $GA_7$) and triapenthenol. The following Examples illustrate the invention.

EXAMPLE 1

Preparation of the copper(II) chloride complex of N-5-(2-methoxypyridyl)cyclopyridyl)cyclopropane carboxamide (Compound No. 1 Table I).

N-5-(2-Methoxypyridyl)cyclopropane carboxamide (2.0g) was dissolved in warm ethanol (12ml) and a solution of copper(II) chloride dihydrate (0.888g) in water (2ml) was added. An olive green precipitate formed immediately and after stirring for 40 minutes the solid was filtered off. The solid was washed with water and then with acetone and was then dried under vacuum to give the desired product (1.952g) with a melting point of 186-188° C. (decomposition).

Elemental analysis for the compound.
Molecular formula $C_{20}H_{24}Cl_2CuN_4O_4$

| Element | Calculated | Found |
| --- | --- | --- |
| C | 46.3% | 46.1% |
| H | 4.66% | 4.84% |
| N | 10.8% | 10.8% |
| Cl | 13.66% | 13.37% |

EXAMPLE 2

The zinc (II) chloride complex of N-5-(2-methoxypyridyl) cyclopropane carboxamide (Compound No. 2 Table I) was prepared using the method given in Example 1. This compound has a melting point of 219-221° C. (decomposition).

Elemental analysis for the compound:
Molecular formula $C_{20}H_{24}Cl_2N_4O_4Zn$

| Element | Calculate | Found |
| --- | --- | --- |
| C | 46.13% | 45.51% |
| H | 4.65% | 4.65% |
| N | 10.76% | 10.84% |
| Cl | 13.6% | 13.55% |

The following are examples of compositions suitable for agricultural and horticultural purposes which can be formulated from the compounds of the invention. Such compositions form another aspect of the invention. Percentages are by weight.

EXAMPLE 3

A composition suitable for use as a seed dressing is prepared by grinding and mixing the three ingredients.

| Compound No. 1 of Table I | 50% |
| --- | --- |
| Mineral oil | 2% |
| China clay | 48% |

EXAMPLE 4

A dustable powder is prepared by grinding and mixing the active ingredient with talc.

| Compound No. 1 of Table I | 5% |
| --- | --- |
| Talc | 95% |

EXAMPLE 5

A suspension concentrate is prepared by ball milling the ingredients to form an aqueous suspension of the ground mixture with water.

| Compound No. 1 of Table I | 40% |
| --- | --- |
| Sodium lignosulphonate | 10% |
| Clay | 1% |
| Water | 49% |

This formulation can be used as a spray by diluting into water or applied directly to seed.

EXAMPLE 6

A wettable powder formulation is made by mixing together and grinding the ingredients until all are thoroughly mixed.

| Compound No. 1 of Table I | 25% |
| --- | --- |
| Sodium lauryl sulphate | 2% |
| Sodium lignosulphonate | 5% |
| Silica | 25% |
| China clay | 43% |

EXAMPLE 7

The compounds were tested against a variety of foliar fungal diseases of plants. The technique employed was as follows.

The plants were grown in John Innes Potting Compost (No 1 or 2) in 4 cm diameter minipots. The test compounds were formulated by bead milling with aqueous Dispersol T which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i. in dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4 = no disease
3 = trace-5% of disease on untreated plants
2 = 6-25% of disease on untreated plants
1 = 26-59% of disease on untreated plants
0 = 60-100% of disease on untreated plants
The results are shown in Table II.

independently 1, 2 or 3 according to valency requirements; and n is 1, 2 or 3.

3. A metal complex

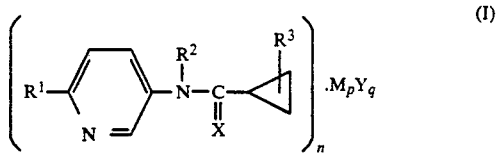

according to claim 1 or 2 wherein $M_pY_q$ is copper (II) chloride or zinc (II) chloride; and n is 2.

4. A fungicidal composition comprising a fungicidally effective amount of a metal complex having the formula:

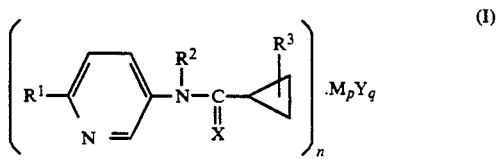

wherein $R^1$ is $C_{1-4}$ alkoxy, $C_{1-4}$ haloalkoxy, or $C_{2-4}$ alkenyloxy; $R^2$ is hydrogen or cyano; $R^3$ is hydrogen or methyl; X is oxygen or sulphur; $M_pY_q$ is a transition metal salt wherein M is a metal cation, Y is an anion and p and q are independently 1, 2 and 3 according to va-

TABLE II

| Compound No | *Puccinia recondita* (wheat) | *Erysiphe graminis* (barley) | *Venturia inaequalis* (apples) | *Pyricularia oryzae* (rice) | *Cercospora arachidicola* (peanut) | *Plasmopara viticola* (vines) |
|---|---|---|---|---|---|---|
| 1 | 4 | 4 | 4 | 3 | 3 | 4 |
| 2 | 4 | 4 | 4 | 0 | 0 | 4 |

We claim:

1. A metal complex having the formula (I):

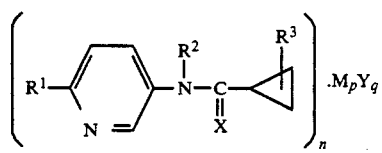

wherein $R^1$ is $C_{1-4}$ alkoxy, $C_{1-4}$ haloalkoxy, or $C_{2-4}$ alkenyloxy; $R^2$ is hydrogen or cyano; $R^3$ is hydrogen or methyl; X is oxygen or sulphur; $M_pY_q$ is a transition metal salt wherein M is a metal cation, Y is an anion and p and q are independently 1, 2 or 3 according to valency requirements; and n is 1 or 2.

2. A metal complex having the formula (I):

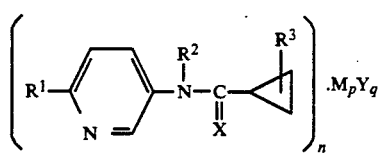

wherein $R^1$ is $C_{1-4}$ alkoxy; $R^2$ and $R^3$ are both hydrogen; X is oxygen; $M_pY_q$ is a transition metal salt wherein M is a copper (II) or zinc (II) cation, Y is a chloride, bromide, iodide, fluoride, nitrate, sulphate, acetate, phosphate, formate, citrate, tartrate, benzoate, borate, lactate or o-benzoic sulphimide anion and p and q are lency requirements; and n is 1 or 2 and a fungicidally acceptable carrier or diluent therefor.

5. A method of combating fungi which comprises applying to plants, to the seeds of plants or to the locus of the plants or seeds a fungicidally effective amount of a metal complex having the formula:

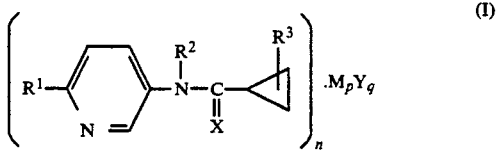

wherein $R^1$ is $C_{1-4}$ alkoxy, $C_{1-4}$ haloalkoxy, or $C_{2-4}$ alkenyloxy; $R^2$ is hydrogen or cyano; $R^3$ is hydrogen or methyl; X is oxygen or sulphur; $M_pY_q$ is a transition metal salt wherein M is a metal cation, Y is an anion and p and q are independently 1, 2 or 3 according to valency requirements; and n is 1 or 2 and a fungicidally acceptable carrier or diluent therefor.

6. A metal complex according to claim 1 wherein $R^1$ is methoxy; $R^2$ and $R^3$ are both hydrogen; X is oxygen; $M_pY_q$ is copper (II) or zinc (II); and Y is chloride, bromide, iodide, fluoride, nitrate, sulphate, acetate, phosphate, formate, citrate, tartrate, benzoate, borate, lactate or o-benzoic sulphimide anion.

7. A metal complex according to claim 2 wherein $R^1$ is methoxy.

8. A fungicidal composition according to claim 4 wherein $R^1$ is methoxy; $R^2$ and $R^3$ are both hydrogen; X is oxygen; $M_pY_q$ is copper (II) chloride or zinc (II) chloride; and n is 2.

9. A fungicidal composition according to claim 4 wherein said metal complex is the copper (II) chloride complex of N-5-(2-methoxypyridyl) cyclopropane carboxamide.

10. A fungicidal composition according to claim 4 wherein said metal complex is the zinc (II) chloride complex of N-5-(2-methoxypyridyl) cyclopropane carboxamide.

11. A method of claim 5 wherein said metal complex is the copper (II) chloride complex of N-5-(2-methoxypyridyl) cyclopropane carboxamide.

12. A method of claim 5 wherein said metal complex is the zinc (II) chloride complex of N-5-(2-methoxypyridyl) cyclopropane carboxamide.

* * * * *